United States Patent
Mori et al.

(10) Patent No.: US 12,042,567 B2
(45) Date of Patent: *Jul. 23, 2024

(54) DISINFECTION SYSTEM OF CONTACT LENS

(71) Applicant: MENICON CO., LTD., Nagoya (JP)

(72) Inventors: Osamu Mori, Kasugai (JP); Yukihiro Kojima, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/716,284

(22) Filed: Apr. 8, 2022

(65) Prior Publication Data

US 2022/0226535 A1    Jul. 21, 2022

Related U.S. Application Data

(63) Continuation of application No. 15/930,591, filed on May 13, 2020, now Pat. No. 11,331,404, which is a continuation of application No. 16/164,256, filed on Oct. 18, 2018, now abandoned, which is a continuation of application No. 15/250,413, filed on Aug. 29, 2016, now Pat. No. 10,137,218, which is a continuation of application No. 13/311,712, filed on Dec. 6, 2011, now Pat. No. 9,427,488, which is a continuation of application No. PCT/JP2009/002993, filed on Jun. 29, 2009.

(51) Int. Cl.
*A61L 12/12* (2006.01)
*A61L 12/08* (2006.01)

(52) U.S. Cl.
CPC ............ *A61L 12/128* (2013.01); *A61L 12/086* (2013.01)

(58) Field of Classification Search
CPC ..... A61L 12/128; A61L 12/086; A61L 12/124
USPC ...................................... 422/28, 30
See application file for complete search history.

(56) References Cited

U.S. PATENT DOCUMENTS

| | | | |
|---|---|---|---|
| 3,912,451 A | 10/1975 | Gaglia, Jr. | |
| 4,521,375 A | 6/1985 | Houlsby | |
| 4,568,517 A | 2/1986 | Kaspar et al. | |
| 4,812,173 A | 3/1989 | Tsao et al. | |
| 4,889,689 A | 12/1989 | Tsao | |
| 4,986,963 A | 1/1991 | Corcoran et al. | |
| 5,270,002 A | 12/1993 | Neff, II et al. | |
| 5,281,353 A | 1/1994 | Park et al. | |
| 5,556,480 A | 9/1996 | Rontome et al. | |
| 5,660,862 A | 8/1997 | Park et al. | |
| 6,338,847 B1 | 1/2002 | Thomas | |
| 6,790,409 B1 | 9/2004 | Nakamura et al. | |
| 9,427,488 B2 | 8/2016 | Mori et al. | |
| 10,137,218 B2 * | 11/2018 | Mori | A61L 12/128 |
| 11,331,404 B2 * | 5/2022 | Mori | A61L 12/128 |
| 2003/0125221 A1 | 7/2003 | Mowrey-McKee et al. | |
| 2003/0153622 A1 | 8/2003 | Hozumi et al. | |
| 2004/0038956 A1 | 2/2004 | Nakada et al. | |
| 2004/0234569 A1 | 11/2004 | Nakada et al. | |
| 2009/0239954 A1 | 9/2009 | Collins et al. | |

FOREIGN PATENT DOCUMENTS

| | | |
|---|---|---|
| CN | 1197397 A | 10/1998 |
| EP | 0 265 381 A2 | 4/1988 |
| EP | 1 557 180 A1 | 7/2005 |
| JP | S63-102760 A | 5/1988 |
| JP | S63-274602 A | 11/1988 |
| JP | H03-278837 A1 | 12/1991 |
| JP | H04-507052 A | 12/1992 |
| JP | 2004-024715 A1 | 1/2004 |
| JP | 2004-141546 A1 | 5/2004 |
| JP | 2005-211545 A1 | 8/2005 |
| WO | 1990/14848 A1 | 12/1990 |
| WO | 97/11722 A1 | 4/1997 |
| WO | 2002/36922 A1 | 5/2002 |
| WO | 2007/090461 A1 | 8/2007 |

OTHER PUBLICATIONS

Dec. 12, 2013 Office Action issued in Chinese Patent Application No. 200980160186.
Nov. 15, 2012 Extended European Search Report issued in European Patent Application No. 09846757.4.
Martin, H. et al. "Synergism between hydrogen peroxide and seventeen acids against five agri-food-borne fungi and one yeast strain". Journal of Applied Microbiology. vol. 113, pp. 1451-1460, 2012.
Jones, Lyndon et al. "Soft Contact Lens Solutions Review: Part 2: Modern-Generation Care System". Optometry in Practice. vol. 9, pp. 43-62, 2008.
Hughes, Reanne et al. "Comparison of Hydrogen Peroxide Contact Lens Disinfection Systems and Solutions against Acanthamoeba polyphaga". Antimicrobial Agents and Chemotherapy. vol. 45, No. 7, pp. 2038-2043, 2001.
Oct. 8, 2015 Extended European Search Report issued in European Application No. 15170639.7.

* cited by examiner

*Primary Examiner* — Timothy C Cleveland
(74) *Attorney, Agent, or Firm* — Oliff PLC

(57) ABSTRACT

A disinfection system of a contact lens comprising immersing the contact lens in a disinfecting solution containing hydrogen peroxide in a concentration of 1 to 10% and neutralizing the hydrogen peroxide in the disinfecting solution through contact with a metal catalyst, where the disinfecting solution contains an organic carboxylic acid or a salt of the organic carboxylic acid, the organic carboxylic acid having a structure in which a hydroxyl group and a carboxyl group are bonded to one carbon atom; the disinfecting solution is adjusted to have a pH of 6 to 8; and the disinfecting solution after the neutralization is adjusted to have an osmotic pressure of 250 to 350 mOsm.

18 Claims, No Drawings

DISINFECTION SYSTEM OF CONTACT LENS

This application is a continuation of U.S. patent application Ser. No. 15/930,591, filed on May 13, 2020, which is a continuation of U.S. patent application Ser. No. 16/164,256, filed on Oct. 18, 2018, which is a continuation of U.S. patent application Ser. No. 15/250,413, filed on Aug. 29, 2016, which is a continuation of U.S. patent application Ser. No. 13/311,712, filed on Dec. 6, 2011, which is a continuation of the International Application No. PCT/JP2009/002993 filed on Jun. 29, 2009. The entireties of which are incorporated herein by reference.

TECHNICAL FIELD

The present invention relates to a disinfection system of contact lenses, and particularly to a disinfection system in which a hydrogen peroxide-containing disinfecting solution for an immersion treatment of contact lenses is effectively neutralized with a metal catalyst.

BACKGROUND ART

As one of methods for chemically cleaning and disinfecting contact lenses, particularly soft contact lenses, there has hitherto been widely known a disinfection system using hydrogen peroxide. The hydrogen peroxide used therein is an effective disinfectant, and particularly attractive for disinfection of the contact lenses, because a decomposed product thereof is only water. However, such hydrogen peroxide is an active oxidant, so that the hydrogen peroxide should be completely removed from the contact lenses that were subjected to a disinfection treatment, before the contact lenses are worn again on the eye.

In a chemical disinfection method using such hydrogen peroxide, in order to obtain a desired disinfection effect, the hydrogen peroxide is generally required to have a concentration as high as about 3%, and a neutralization treatment for decomposing and detoxifying the hydrogen peroxide remaining on surfaces or in the insides of the contact lenses should be performed after the disinfection. The reason for this is that the hydrogen peroxide inevitably remains on the surfaces or in the insides of the contact lenses after disinfection, because the hydrogen peroxide is used at a relatively high concentration. The hydrogen peroxide remaining on or in the lenses may seriously damage the eyes, even if the amount is small.

Thus, to the contact lenses subjected to the disinfection treatment by using the hydrogen peroxide, the neutralization treatment is conventionally applied. Specifically, the remaining hydrogen peroxide is removed by rinsing with a physiological saline, or completely decomposed and removed by using a metal catalyst such as platinum, a reducing agent such as sodium sulfite, sodium thiosulfate or pyruvic acid, an enzyme catalyst such as catalase or peroxidase, or the like. However, such a neutralization treatment generally makes a disinfection treatment operation of the contact lenses very cumbersome and complicated.

Accordingly, in order to easily perform the disinfection operation of the contact lenses using such hydrogen peroxide, JP-T-4-507052 discloses a vertical type contact lens case as an apparatus for sterilizing the contact lenses. In such a contact lens case, a hydrogen peroxide-containing sterilizing solution is contained, and the contact lenses to be treated and a catalyst agent are disposed therein so as be in contact with the sterilizing solution. As a result, the contact lenses are disinfected or sterilized, while a neutralization treatment is performed in which the hydrogen peroxide in the sterilizing solution is decomposed with the catalyst agent. The neutralization rate of the hydrogen peroxide in such a sterilizing solution depends on the amount of catalyst (metal) in the catalyst agent. In order to completely remove the hydrogen peroxide effectively from the contact lenses, the neutralization efficiency needs to be increased by improving the neutralization rate without influencing a disinfecting effect on the lenses. For this purpose, the amount of the catalyst metal needs to be increased. Further, the catalyst agent (catalyst metal) used herein needs to be replaced with a new one at a predetermined time intervals in order to assure the safety, for example. Accordingly, in the disinfection system using the hydrogen peroxide, it is a major object to reduce the amount of the catalyst metal in terms of cost reduction.

Further, JP-A-63-274602 discloses a stabilized hydrogen peroxide solution including a hydrogen peroxide solution, and a peroxide stabilizer composed of a predetermined sulfonic acid compound and a secondary peroxide stabilizer such as glycerin or polyvinyl alcohol, which are added to the hydrogen peroxide solution. It also discloses that the sterilization by heat can be performed in combination by the use of this stabilized hydrogen peroxide solution as a disinfecting solution of contact lenses, resulting in the reduction of time for immersing lens materials in the disinfecting solution. However, it discloses that the hydrogen peroxide must be removed after the disinfection treatment, and in order to remove it, the contact lenses are rinsed or a known hydrogen peroxide-decomposing material is allowed to be in contact with the solution, after the disinfection treatment.

Furthermore, WO2002/26922 proposes a technique of inhibiting foaming at the time of a disinfection operation of contact lenses by allowing a surfactant composed of a block copolymer having a hydrophobic block and a hydrophilic block to be contained in a contact lens disinfecting solution containing an effective disinfecting amount of hydrogen peroxide. In addition, JP-A-3-278837 discloses a method of disinfecting contact lenses by using a hydrogen peroxide-decomposing catalyst in which manganese oxide, cobalt oxide or copper oxide is carried on an inorganic carrier. However, these Patent Documents do not disclose in any way that the disinfection of the contact lenses is effectively performed by increasing the neutralization rate of the hydrogen peroxide in the disinfecting solution to improve its neutralization efficiency by using a specific composition of the disinfecting solution, in other words, by adding specific components to the disinfecting solution.

As described above, various disinfection systems of contact lenses using hydrogen peroxide solutions have conventionally been proposed. However, none of them has proposed or reported any composition of solution for increasing the neutralization rate of hydrogen peroxide to improve its neutralization efficiency, while securing the effective disinfection effect by a hydrogen peroxide-containing solution (disinfecting solution).

SUMMARY OF INVENTION

The present invention has been made in the light of the situations described above. It is therefore an object of the present invention to provide a disinfection system of a contact lens using hydrogen peroxide, in which neutralization efficiency of such hydrogen peroxide is increased to reduce the amount of metal used in a metal catalyst, thereby advantageously saving resource.

To achieve the object described above and other objects which will be understood from the description of the entire specification, the present invention can be suitably carried out in various aspects described below, and the respective aspects described below can also be employed in any combination. It is to be understood that the aspects and technical features of the present invention are not limited to those described below and should be recognized on the basis of the concept of the invention as disclosed in the entire specification.

(1) A disinfection system of a contact lens including immersing the contact lens in a disinfecting solution containing hydrogen peroxide in a concentration of 1 to 10% and neutralizing the hydrogen peroxide in the disinfecting solution through contact with a metal catalyst, the disinfection system comprising the steps of: adding one of an organic carboxylic acid and a salt thereof into the disinfecting solution, the organic carboxylic acid having a structure in which a hydroxyl group and a carboxyl group are bonded to one carbon atom; adjusting a pH of the disinfecting solution to 6 to 8; and adjusting an osmotic pressure of the disinfecting solution after the neutralization to 250 to 350 mOsm.

(2) The disinfection system of a contact lens according to the above aspect (1), where the pH of the disinfecting solution is adjusted by adding one of an acid and an alkaline agent into an aqueous hydrogen peroxide solution, together with the organic carboxylic acid or the salt thereof.

(3) The disinfection system of a contact lens according to the above aspect (1) or (2), where the organic carboxylic acid is glycolic acid.

(4) The disinfection system of a contact lens according to the above aspect (1) or (2), where the organic carboxylic acid is tartaric acid.

(5) The disinfection system of a contact lens according to the above aspect (1) or (2), where the organic carboxylic acid is citric acid.

(6) The disinfection system of a contact lens according to any one of the above aspects (1) to (5), where the organic carboxylic acid or the salt thereof is contained at a concentration of at least 0.1% or more.

(7) The disinfection system of a contact lens according to any one of the above aspects (1) to (6), where the disinfecting solution further contains a chelating agent.

(8) The disinfection system of a contact lens according to the above aspect (7), where the chelating agent is at least one selected from the group consisting of EDTA, a salt thereof, etidronic acid, and a salt thereof.

(9) The disinfection system of a contact lens according to any one of the above aspects (1) to (8), where the metal catalyst is a metal film catalyst.

(10) The disinfection system of a contact lens according to any one of the above aspects (1) to (9), where the disinfecting solution further contains at least one of surfactant and a nonionic tonicity agent.

(11) The disinfection system of a contact lens according to any one of the above aspects (1) to (10), where the metal catalyst is contained in a predetermined treatment container for contact lens disinfection, and the disinfecting solution is contained in the treatment container to allow the metal catalyst be in contact with the disinfecting solution.

As described above, in the disinfection system of a contact lens in accordance with the present invention, the organic carboxylic acid or salt thereof, which has the specific structure in which the hydroxyl group and the carboxyl group are bonded, is added into the disinfecting solution containing the hydrogen peroxide, and the pH of the disinfecting solution is adjusted to 6 to 8, so that the contact lens is effectively disinfected by being immersed into the disinfecting solution, and the neutralization rate of the hydrogen peroxide in the disinfecting solution is effectively improved, which results in the improvement of the neutralization efficiency of the hydrogen peroxide. As a result, the amount of metal used in the metal catalyst, which is necessary for completing the neutralization within a desired period of time, can be reduced, thereby advantageously saving the resource of the catalyst metal, which is valuable. Further, the disinfection system can be provided at a lower cost by saving the catalyst metal.

Moreover, in the disinfection system of the present invention, the disinfecting solution after the neutralization treatment is constituted so as to have an osmotic pressure of 250 to 350 mOsm. Therefore, the contact lens after the neutralization treatment can be worn on the eye as it is, without performing a cleaning treatment such as rinsing. In particular, when the disinfecting solution is prepared by containing the surfactant and/or the nonionic tonicity agent, the characteristics of direct wearing of the contact lens after the disinfection are more advantageously exhibited.

DETAILED DESCRIPTION OF THE INVENTION

In the disinfection system of a contact lens in accordance with the present invention, the hydrogen peroxide-containing disinfecting solution into which the contact lens to be disinfected is immersed is prepared so as to have a hydrogen peroxide concentration of 1 to 10% (on weight basis). The amount of the hydrogen peroxide smaller than the above-described range may cause a problem that the disinfection effect due to the hydrogen peroxide cannot be sufficiently exhibited. Conversely, the amount of the hydrogen peroxide exceeding the above-described range, although the excellent disinfection effect is obtained, may cause problems that the neutralization treatment requires much more time, the amount of metal catalyst used for decomposition and neutralization of the hydrogen peroxide is increased, and the hydrogen peroxide becomes liable to remain on a surface or in the inside of the contact lens due to the insufficient neutralization treatment, resulting in an adverse effect on the eye. In order to advantageously avoid these problems, a hydrogen peroxide concentration of 2 to 6% by weight is particularly suitably employed.

Further, the metal catalyst which carries out the neutralization treatment, in which the hydrogen oxide is detoxified to eliminate adverse effect on the eye, by contacting and decomposing the hydrogen peroxide contained in the disinfecting solution, is appropriately selected from various known metal catalysts which have hitherto been used for the decomposition and neutralization treatment of the hydrogen peroxide. For example, platinum is preferably used as a metal catalyst. In addition, metals such as palladium, silver, copper, manganese, cobalt and aluminum or oxides of such metals can also be used, for example.

These metals or the oxides thereof can be formed as the metal catalysts in the same catalyst form as the conventional one. In the present invention, a metal film catalyst, in other words, the catalyst formed by adhering the above-mentioned metal or the oxide thereof in film form to a predetermined substrate is particularly advantageously used. Specifically, such a metal film catalyst is obtained by a known film forming technique, i.e., by plating or sputtering the above-mentioned catalyst metal on a surface of the substrate having various shapes such as a disk and a flat plate having a predetermined size. The metal film catalyst is disposed in the disinfecting solution and is allowed to be in contact with the hydrogen peroxide present in the disinfecting solution. Further, as a material of such a substrate, at least one selected from the group consisting of a plastic, a metal, a glass, a ceramic and an ion-exchange resin is suitably used. Furthermore, examples of plastic materials include an acrylonitrile-butadiene-styrene (ABS) resin, polyurethane, modified polyphenylene ether, polystyrene, polycarbonate, polyethylene terephthalate (PET), polybutylene terephthalate (PBT), polyvinyl chloride, polyetherimide, polysulfone, polymethyl methacrylate and copolymer resins thereof.

Then, in the present invention, the specific organic carboxylic acid or salt thereof, having a structure in which a hydroxyl group and a carboxyl group are bonded to one carbon atom, is allowed to be contained in such a disinfecting solution, and the pH of such a disinfecting solution is adjusted to 6 to 8, thereby effectively performing the above-mentioned contact lens disinfection and the neutralization treatment with the metal catalyst. That is to say, while the disinfection treatment is effectively performed with the hydrogen peroxide, the neutralization rate of the hydrogen peroxide with the metal catalyst can be effectively increased, which results in advantageous improvement of its neutralization efficiency.

The specific organic carboxylic acid or salt thereof used herein has a structure in which a hydroxyl group and a carboxyl group are bonded to one carbon atom, thereby effectively contributing to the acceleration of the decomposition and neutralization of the hydrogen peroxide. Example of the organic carboxylic acid include glycolic acid, malic acid, tartaric acid and citric acid. In order to achieve the object of the present invention, glycolic acid is advantageously used.

Then, such a specific organic carboxylic acid is generally contained in the disinfecting solution at a rate of at least 0.1% weight basis in order to advantageously improve the neutralization efficiency of the hydrogen peroxide, which is desired in the present invention. On the other hand, the upper limit of the content of such a specific organic carboxylic acid is generally about 5%. However, depending on the kind of the carboxylic acid, the concentration thereof is appropriately determined so that the disinfecting solution after the neutralization treatment has a desired osmotic pressure.

Further, in the present invention, the pH of the disinfecting solution containing the above-mentioned specific organic carboxylic acid or salt thereof is adjusted to 6 to 8. To adjust pH, an acid or an alkaline agent is used. In particular, in the preparation of the hydrogen peroxide-containing disinfecting solution, a proper commercially available aqueous hydrogen peroxide solution is generally used, and such an aqueous hydrogen peroxide solution is maintained under an acidic condition for stability of the solution. Accordingly, in the present invention, a known proper alkaline agent such as sodium hydroxide or potassium hydroxide is advantageously added together with the above-mentioned organic carboxylic acid or salt thereof to perform the pH adjustment of such an aqueous hydrogen peroxide solution, thereby adjusting the pH of the resulting disinfecting solution to 6 to 8.

As described above, the disinfection of the contact lens is performed by using the disinfecting solution of the present invention with the pH adjusted to 6 to 8, while the hydrogen peroxide in the disinfecting solution is neutralized with the metal catalyst, whereby the neutralization rate thereof can be effectively increased, resulting in the improvement of the neutralization efficiency. Further, the pH of the hydrogen peroxide after the neutralization becomes nearly neutral, so that there is also an advantage of less irritation even when the lens after the treatment is directly placed on the eye. The pH of the disinfecting solution lower than 6 will not sufficiently increase the neutralization rate of the hydrogen peroxide with the metal catalyst, for example. The pH of the disinfecting solution exceeding 8 will decrease the stability of the disinfecting solution, which fails to provide a sufficient time for application of the disinfecting solution to the disinfection system.

In the present invention, even when the pH of the disinfecting solution is adjusted to 6 to 8, since the above-mentioned specific organic carboxylic acid or salt thereof is present, the stability of the hydrogen peroxide is effectively enhanced by a chelate action thereof. Accordingly, in the disinfecting solution of the present invention, most of the hydrogen peroxide is not decomposed and present, particularly at a residual rate of 90% or more, even after the elapse of a long period of time after the preparation thereof. Therefore, the disinfecting solution can be advantageously used for the disinfection of the contact lens over a long period of time.

Further, in the disinfection system of a contact lens in accordance with the present invention, the contents of the essential components in the disinfecting solution (unused) used for the disinfection and neutralization of the contact lens and the amounts of addition components to be added as necessary are adjusted, and a known tonicity agent is further added and contained as necessary, so that the disinfecting solution after the neutralization treatment has an osmotic pressure of 250 to 350 mOsm. The adjustment of the osmotic pressure of the disinfecting solution after the neutralization treatment allows the osmotic pressure of the disinfecting solution to be almost equivalent to the osmotic pressure of the tear fluid, so that it is possible to wear the contact lens after the disinfection and neutralization treatments on the eye as it is. Even in the case where the disinfecting solution enter in the eye by wearing the contact lens with the disinfecting solution remaining on and adhering to a lens surface thereof, irritation to the eye of a wearer can be advantageously reduced, and the adverse effect on the eye can be advantageously avoided.

In the disinfecting solution used in the present invention, known various addition components used in the general preparation of disinfecting solutions, for example, a chelating agent, a surfactant, a tonicity agent, a buffer, a thickener, a preservative and the like, may be contained as needed, either alone or as a combination of two or more thereof, in addition to the hydrogen peroxide and the specific organic carboxylic acid or salt thereof as the essential components. However, it is necessary that all of those respective components are safe to the living body and ophthalmic physiologically acceptable, and do not impede the functions and effects of the present invention as described above. Further, each of the components is used within the quantitative range that does not impair the effects.

In particular, the chelating agent improves the stability of the disinfecting agent of the present invention to advantageously achieve long-term reservation thereof. At least one of EDTA (ethylenediaminetetraacetic acid), a salt thereof, etidronic acid, and a salt thereof is advantageously used. The chelating agent is generally contained in the disinfecting solution at a concentration of about 0.01 to 0.5% by weight.

The surfactant is further contained for the cleaning of the contact lens, separately from the disinfection of the contact lens. As such surfactants, there can be advantageously employed all of known anionic, nonionic, amphoteric and cationic surfactants which have hitherto been used in contact lens solutions and the like. By the addition of the surfactant, an effective cleaning effect such as a lipid-removing action is imparted to the disinfecting solution. Among others, in the present invention, nonionic surfactants are preferably used. Examples of the nonionic surfactant include polyethylene glycol ethers of higher alcohols, polyethylene glycol esters of higher fatty acids, polyglycerol esters of fatty acids, polyethylene glycol ethers of alkyl phenols, polyethylene glycol sorbitan alkyl esters, polyoxyethylene-polyoxypropylene glycols (poloxamers), and ethylenediamine tetrapolyoxyethylene polyoxypropylenes (poloxamines). Of these, block copolymers of polyoxyethylene and polyoxypropylene or derivatives thereof (poloxamers or poloxamines) are particularly advantageously used.

Further, the tonicity agent is added in order to easily perform the adjustment of the osmotic pressure of the disinfecting solution before the disinfection treatment of the contact lens, and eventually after the disinfection thereof. Known various tonicity agents which have been generally used in contact lens solutions are appropriately used. Of these, known nonionic tonicity agents such as propylene glycol, glycerol and saccharide s are particularly advantageously used in the present invention. By the addition of such a nonionic tonicity agent into the disinfecting solution, lipophilicity of the solution is increased, and the occurrence of ocular irritation can be more advantageously inhibited, thereby obtaining more excellent sense of use. Of these, propylene glycol is more suitably employed, because it increases the viscosity of the solution, advantageously resulting in the reduction in the occurrence of ocular irritation.

In the preparation of the disinfecting solution of the present invention, no special method is required in any way. As in the preparation of the conventional disinfecting solution for contact lenses, the desired disinfecting solution can be easily obtained by adding or dissolving the respective components in an aqueous medium, without regard to the addition order, or sequentially or concurrently, or in appropriate combination thereof. It is to be understood that, in the preparation of the disinfecting solution, other than water itself such as purified water or distilled water, any known aqueous solution such as a physiological saline, a contact lens storing solution or a cleaning solution may be used as the aqueous medium, as long as it is a solution mainly composed of water.

Then, in the present invention, the contact lens to be subjected to the disinfection treatment is immersed in the disinfecting solution prepared in this way, thereby disinfecting the contact lens with the hydrogen peroxide. Then, after such a disinfection treatment has been performed for a period of time that is enough to disinfect the contact lens, the metal catalyst is allowed to be in contact with the disinfecting solution in which the contact lens is immersed, in order to neutralize the hydrogen peroxide so that the hydrogen peroxide does not remain in the disinfecting solution. Accordingly, the neutralization treatment is performed through contact with the hydrogen peroxide. As procedures for the disinfection treatment and the neutralization treatment, any known procedures are appropriately employed.

For example, in addition to the procedure in which the disinfection treatment and the neutralization treatment are performed by immersing the contact lens and the metal catalyst concurrently or sequentially in the disinfecting solution in a state where a predetermined amount of the disinfecting solution is contained in a predetermined treatment container, any known procedures may be suitably employed, such as a procedure in which the disinfection treatment and the neutralization treatment are performed in parallel with each other by pouring the disinfecting solution in a treatment container in a state where the contact lens and the metal catalyst are arranged in the treatment container, a procedure in which the treatments are performed by allowing the disinfecting solution to be contained in a treatment container in a state where one of the contact lens and the metal catalyst is arranged in the treatment container and thereafter the other one of the contact lens and the metal catalyst is immersed in the disinfecting solution to be in contact therewith.

Further, as a structure of the treatment container, a known container for a contact lens treatment using a solution can be appropriately selected and used. Specifically, a sterilizing device having the structure as disclosed in the foregoing JP-T-4-507052 can be used as it is. In any case, the treatment container having any structure may be employed as long as the contact lens and the metal catalyst can be immersed into and contacted with the disinfecting solution in a state where the container contains the contact lens and the metal catalyst.

Further, the kind of the contact lens to be disinfected in such a disinfection system in accordance with the present invention is not limited. For example, all kinds of contact lenses may be disinfected irrespective of water-containing or non-water-containing and soft or hard materials. The present invention is applicable to all contact lenses made from any material. However, conventional disinfection systems using the hydrogen peroxide are used to disinfect soft contact lenses, so that in the present invention, the disinfection system is also mainly applied to the disinfection of the soft contact lenses. Here, the soft contact lenses composed of water-containing hydrogels are known. As a typical example of such contact lenses, there is one formed of a polymer or copolymer of a hydrophilic monomer such as 2-hydroxyethyl methacrylate, N,N-dimethylacrylamide, N-vinyl-2-pyrrolidone or methacrylic acid. In recent years, the soft contact lenses also include contact lenses composed of silicone hydrogels, which are copolymers produced by copolymerizing silicone-containing hydrophobic monomers in combination with these hydrophilic monomers. The present invention is also applicable to such soft contact lenses.

After the application of the disinfection system in accordance with the present invention, the contact lens that was subjected to the disinfection treatment is generally taken out of the disinfecting solution and worn on the eye. Since the neutralization treatment using the metal catalyst is performed to the hydrogen peroxide in the disinfecting solution, the amount of the hydrogen peroxide remaining in the disinfecting solution is extremely reduced, and the hydrogen peroxide adhering to the contact lens or remaining in the lens is also negligible. Accordingly, even when the contact lens taken out of the disinfecting solution is worn on the eye as it is, it can be safely worn without causing problem.

EXAMPLES

To further clarify the present invention, some examples of the invention will be described. It is to be understood that the invention is not limited to the details of illustrated examples and the forgoing description, but may be embodied with various changes, modifications, and improvements, which may occur to those skilled in the art without departing from the scope of the invention.

—Preparation of Disinfecting Solution Specimens—

A commercially available aqueous hydrogen peroxide solution was diluted with distilled water to various concentrations indicated in the following Tables 1 to 4, and various addition components indicated in these Tables were added to be contained, thereby preparing various disinfecting solution specimens of Examples 1 to 18 and Comparative Examples 1 to 14. Further, in the preparation of such disinfecting solution specimens, hydrochloric acid was used as an acid and caustic soda was used as an alkaline agent to obtain the disinfecting solution specimens having desired pH values.

The addition components in the following Tables were added and contained as follows: a poloxamer (polyoxyethylene-polyoxypropylene glycol) as a nonionic surfactant; EDTA·2Na (ethylenediamine tetraacetic acid disodium salt) and etidronic acid as chelating agents; PG (propylene glycol) as a nonionic tonicity agent; glycolic acid, tartaric acid and citric acid as specific organic carboxylic acid components of the present invention; and NaCl, boric acid, phosphoric acid, tris, taurine and aspartic acid as other auxiliary components such as a buffer.

Further, in order to evaluate stability of the respective solutions, the respective disinfecting solution specimens thus prepared were stored under accelerating conditions (40° C.×3 months), and thereafter, the residual rate of hydrogen peroxide in the respective disinfecting solution specimens was measured and determined by "the titration method of oxydol" described in The Japanese Pharmacopoeia. The results thereof are shown together in the following Tables 1 to 4. "Excellent" denotes that the residual rate thereof was 95% or more, "Good" denotes that the residual rate was from 90% to less than 95%, "Fair" denotes that the residual rate was from 80% to less than 90%, and "Poor" denotes that the residual rate was less than 80%.

TABLE 1

| | Addition Components | Examples | | | | | | | | |
|---|---|---|---|---|---|---|---|---|---|---|
| | | 1 | 2 | 3 | 4 | 5 | 6 | 7 | 8 | 9 |
| Disinfecting Solution Composition [% by weight] | Hydrogen Peroxide | 3.4 | 3.4 | 3.4 | 3.4 | 5.3 | 8.5 | 3.4 | 3.4 | 3.4 |
| | EDTA·2Na | — | 0.1 | 0.1 | 0.1 | 0.1 | 0.1 | 0.1 | 0.1 | 0.1 |
| | Glycolic Acid | 1 | 1 | 1 | 1 | 1 | 1 | 1 | — | — |
| | Tartaric Acid | — | — | — | — | — | — | — | 1 | — |
| | Citric Acid | — | — | — | — | — | — | — | — | 1 |
| | NaCl | — | — | — | — | — | — | — | 0.35 | 0.45 |
| Disinfecting Solution pH (before Neutralization) | | 7.4 | 6 | 7.4 | 7.4 | 7.4 | 7.4 | 8 | 7.4 | 7.4 |
| Disinfecting Solution Stability (Acceleration) | $H_2O_2$ Residual Rate [%] | 90 | 100 | 98 | 99 | 96 | — | 97 | 94 | 92 |
| | Evaluation | Good | Excellent | Excellent | Excellent | Excellent | — | Excellent | Good | Good |

TABLE 2

| | Addition Components | Examples | | | | | | | | |
|---|---|---|---|---|---|---|---|---|---|---|
| | | 10 | 11 | 12 | 13 | 14 | 15 | 16 | 17 | 18 |
| Disinfecting Solution Composition [% by weight] | Hydrogen Peroxide | 3.4 | 3.4 | 3.4 | 3.4 | 3.4 | 3.4 | 3.4 | 3.4 | 3.4 |
| | Poloxamer | 0.08 | — | 0.08 | 0.08 | 0.08 | 0.08 | 0.08 | 0.08 | 0.08 |
| | EDTA·2Na | — | — | 0.1 | 0.1 | 0.1 | 0.1 | — | 0.1 | 0.1 |
| | Etidronic Acid | — | 0.02 | 0.02 | 0.02 | 0.02 | — | 0.02 | 0.02 | 0.02 |
| | PG | 0.50 | — | 0.50 | — | — | 0.50 | 0.50 | 0.50 | 0.50 |
| | Glycolic Acid | 0.70 | 1.00 | 0.70 | 0.70 | 0.70 | 0.60 | 1.00 | — | 0.70 |
| | Tartaric Acid | — | — | — | — | — | — | — | 1 | — |
| | NaCl | — | — | — | 0.20 | 0.20 | — | — | 0.10 | — |
| Disinfecting Solution pH (before Neutralization) | | 7.4 | 7.4 | 7.4 | 7.4 | 7.4 | 7.4 | 7.4 | 7.4 | 7.4 |
| Disinfecting Solution Stability (Acceleration) | $H_2O_2$ Residual Rate [%] | 92 | 97 | 100 | 99 | 99 | 97 | 96 | 95 | 100 |
| | Evaluation | Good | Excellent | Excellent | Excellent | Excellent | Excellent | Excellent | Good | Excellent |

TABLE 3

| | Addition Components | Comparative Examples | | | | | |
|---|---|---|---|---|---|---|---|
| | | 1 | 2 | 3 | 4 | 5 | 6 |
| Disinfecting Solution Composition [% by weight] | Hydrogen Peroxide | 3.4 | 3.4 | 3.4 | 12 | 3.4 | 3.4 |
| | EDTA·2Na | — | 0.1 | 0.1 | 0.1 | 0.1 | — |
| | Etidronic Acid | 0.02 | — | — | — | 0.02 | 0.02 |
| | PG | — | — | — | — | 0.50 | 0.50 |
| | Glycolic Acid | 1.00 | 1.00 | 1.00 | 1.00 | 0.45 | 1.20 |

TABLE 3-continued

| | Addition Components | Comparative Examples | | | | | |
|---|---|---|---|---|---|---|---|
| | | 1 | 2 | 3 | 4 | 5 | 6 |
| Disinfecting Solution pH (before Neutralization) | | 2 | 4 | 9 | 7.4 | 7.4 | 7.4 |
| Disinfecting Solution Stability (Acceleration) | H₂O₂ Residual Rate [%] | 98 | 97 | 68 | — | 98 | 96 |
| | Evaluation | Excellent | Excellent | Poor | — | Excellent | Excellent |

TABLE 4

| | Addition Components | Comparative Examples | | | | | | | |
|---|---|---|---|---|---|---|---|---|---|
| | | 7 | 8 | 9 | 10 | 11 | 12 | 13 | 14 |
| Disinfecting Solution Composition [% by weight] | Hydrogen Peroxide | 3.4 | 3.4 | 3.4 | 3.4 | 3.4 | 3.4 | 3.4 | 3.4 |
| | Poloxamer | — | — | — | — | — | 0.08 | 0.08 | — |
| | EDTA·2Na | 0.1 | 0.1 | 0.1 | 0.1 | — | 0.1 | 0.1 | 0.1 |
| | Etidronic Acid | — | — | — | — | — | 0.02 | 0.02 | — |
| | PG | — | — | — | — | — | 0.50 | 0.50 | — |
| | NaCl | 0.30 | 0.55 | 0.35 | 0.55 | 0.35 | 0.15 | 0.15 | — |
| | Boric Acid | 1 | — | — | — | — | — | — | — |
| | Phosphoric Acid | — | 1 | — | — | — | — | — | — |
| | Tris | — | — | 1 | — | — | — | — | — |
| | Taurine | — | — | — | 1 | — | — | — | — |
| | Aspartic Acid | — | — | — | — | 1 | 1 | 1 | — |
| Disinfecting Solution pH (before Neutralization) | | 7.4 | 7.4 | 7.4 | 7.4 | 7.4 | 7.4 | 7.4 | 7.4 |
| Disinfecting Solution stability (Acceleration) | H₂O₂ Residual Rate [%] | 90 | 86 | 99 | 100 | 75 | 93 | 93 | 100 |
| | Evaluation | Good | Fair | Excellent | Excellent | Poor | Good | Good | Excellent |

In the disinfecting solution specimens prepared as described above, as indicated in Tables 1 to 4 above, it is confirmed that all of the disinfecting solution specimens of Examples 1 to 18 that are in accordance with the present invention are high in the residual rate of hydrogen peroxide and excellent in their solution stability, even when stored under the accelerating conditions (40° C.×3 months). In contrast, in the disinfecting solution specimen of Comparative Example 3 having the solution pH exceeding 8 and the disinfecting solution specimen of Comparative Example 8 or 11 further containing phosphoric acid or aspartic acid, it is confirmed that the residual rate of hydrogen peroxide is decreased to cause a problem in solution stability.

—Disinfection and Neutralization Treatments—

Using the respective disinfecting solution specimens obtained above, disinfection and neutralization treatments of contact lenses were performed. Specifically, a plastic disck that is plated with Pt or Pd (a plactic disck A having a catalyst surface area of about 10.4 cm² or a plastic disk B having a catalyst surface area of about 7.0 cm²) was first placed as a metal catalyst at a bottom portion of a plastic container having a volume of 20 mL, and 10 mL of each of disinfecting solution specimens prepared above was poured therein. Then, a commercially available soft contact lens: Month Wear (group II: manufactured by Menicon Co., Ltd.) or Menicon Focus (group IV: manufactured by Menicon Co., Ltd.) as a test lens was accommodated in a commercially available basket-shaped case (having a basket-like housing portion) for a lens treatment, and immersed together with that case into the disinfecting solution specimen contained in the plastic container, followed by keeping under room temperature for 2 hours, thereby performing the disinfection of the test lens and the neutralization treatment of the disinfecting solution specimen.

For each disinfecting solution specimen present in the plastic container after such disinfection and neutralization treatments, the amount of hydrogen peroxide remaining therein was determined by "the titration method of oxydol" described in The Japanese Pharmacopoeia, and evaluation of the neutralization rate was performed. The evaluation results thereof are shown in the following Tables 5 to 8. "Excellent" denotes that the residual amount thereof was less than 100 ppm, "Good" denotes that the residual amount thereof was 100 ppm to less than 200 ppm, "Fair" denotes that the residual amount thereof was 200 ppm to less than 500 ppm, and "Poor" denotes that the residual amount thereof was 500 ppm or more.

Further, the above-mentioned disinfection and neutralization treatments were performed to the two commercially available soft contact lenses, namely "Month Wear" (manufactured by Menicon Co., Ltd.) belonging to group II and "Menicon Focus" (manufactured by Menicon Co., Ltd.) belonging to group IV, and thereafter, the amount of change in DIA (diameter) of each lens was measured. Then, lens compatibility was evaluated, and the results thereof are shown together in the following Tables 5 to 8. "Good" denotes that the amount of change in DIA of the both of the lenses was within a standard, "Fair" denotes that only one lens was within the standard, and "Poor" denotes that both of the lenses were out of the standard.

TABLE 5

|  | Examples | | | | | | | | |
|---|---|---|---|---|---|---|---|---|---|
|  | 1 | 2 | 3 | 4 | 5 | 6 | 7 | 8 | 9 |
| Metal Catalyst | Pt | Pt | Pt | Pt | Pt | Pt | Pt | Pt | Pt |
| Catalyst Surface Area | A | A | A | B | A | A | A | A | A |
| Neutralization Rate | Excellent | Good | Excellent | Good | Excellent | Good | Excellent | Good | Good |
| Osmotic Pressure after Neutralization [mOsm] | 274 | 290 | 294 | 294 | 294 | 294 | 296 | 283 | 274 |
| Lens Compatibility | Good | Good | Good | Good | Good | Good | Good | Good | Good |

TABLE 6

|  | Examples | | | | | | | | |
|---|---|---|---|---|---|---|---|---|---|
|  | 10 | 11 | 12 | 13 | 14 | 15 | 16 | 17 | 18 |
| Metal Catalyst | Pt | Pt | Pt | Pt | Pt | Pt | Pt | Pt | Pd |
| Catalyst Surface Area | A | A | A | A | B | A | A | A | A |
| Neutralization Rate | Good | Excellent | Good | Good | Good | Good | Excellent | Good | Good |
| Osmotic Pressure after Neutralization [mOsm] | 260 | 279 | 286 | 282 | 282 | 253 | 348 | 276 | 286 |
| Lens Compatibility | Good | Good | Good | Good | Good | Good | Good | Good | Good |

TABLE 7

|  | Comparative Examples | | | | | |
|---|---|---|---|---|---|---|
|  | 1 | 2 | 3 | 4 | 5 | 6 |
| Metal Catalyst | Pt | Pt | Pt | Pt | Pt | Pt |
| Catalyst Surface Area | A | A | A | A | A | A |
| Neutralization Rate | Poor | Fair | Excellent | Poor | Good | Excellent |
| Osmotic Pressure after Neutralization [mOsm] | 150 | 215 | 300 | 294 | 217 | 403 |
| Lens Compatibility | Good | Good | Good | — | Fair | Fair |

TABLE 8

|  | Comparative Examples | | | | | | | |
|---|---|---|---|---|---|---|---|---|
|  | 7 | 8 | 9 | 10 | 11 | 12 | 13 | 14 |
| Metal Catalyst | Pt | Pt | Pt | Pt | Pt | Pt | Pd | — |
| Catalyst Surface Area | A | A | A | A | A | A | A | — |
| Neutralization Rate | Good | Fair | Poor | Poor | Poor | Poor | Poor | Fair |
| Osmotic Pressure after Neutralization [mOsm] | 277 | 275 | 283 | 277 | 255 | 284 | 284 | 18 |
| Lens Compatibility | Poor | Good | Good | Fair | Good | Good | Good | Poor |

As is apparent from the results shown in Tables 5 to 8, in all of Examples 1 to 18 in which the disinfection and neutralization treatments were performed using the disinfecting solution specimens in accordance with the present invention, the sufficient neutralization rates and the sufficient lens compatibility were secured. Further, in Examples 4 and 14 in which the catalyst surface area was about 7.0 cm², the sufficient neutralization rates were secured, which means that the intended disinfection and neutralization treatments using the hydrogen peroxide were realized by using small amount of catalyst metal. Thus, the valuable catalyst metal can be saved and the more inexpensive disinfection system can be advantageously provided.

In contrast, the disinfecting solution specimens of Comparative Examples 1 and 2 having the pH of lower than 6 have insufficient neutralization rates. Thus, in order to reduce the amount of the remaining hydrogen peroxide to such a degree as to become harmless to the eye, a larger amount of catalyst metal is required, or that the treating time should be made longer. Further, if the osmotic pressure of the disinfecting solution specimens after the neutralization treatment is too low (Comparative Examples 5 and 14) or too high (Comparative Example 6), it is impossible to wear the lens on the eye as it is, and a problem in lens compatibility is caused due to changes in size of lenses, after the neutralization treatment. Furthermore, the addition components such as boric acid, phosphoric acid, tris, taurine and aspartic acid which are used as a buffer, for example, in conventional contact lens solution cause a problem in the neutralization rate or lens compatibility, as indicated in the results of Comparative Examples 7 to 13. In the disinfection system in accordance with the present invention, those addition components act as interfering components, so that the addition of such interfering components should be avoided in the present invention.

What is claimed is:

1. A contact lens disinfecting solution, comprising:
   hydrogen peroxide at a concentration of 1 to 10 wt %; and
   at least one of an organic carboxylic acid and a salt thereof which comprises a hydroxyl group and a carboxyl group that are bonded to one carbon atom.

2. The contact lens disinfecting solution of claim 1, wherein the contact lens disinfecting solution has a pH of from 6 to 8.

3. The contact lens disinfecting solution of claim 1, wherein the at least one of an organic carboxylic acid and a salt thereof is present at a concentration of 0.1 to 5 wt %.

4. The contact lens disinfecting solution of claim 1, wherein the at least one of an organic carboxylic acid and a salt thereof is present at a concentration of 0.1 to 1 wt %.

5. The contact lens disinfecting solution of claim 1, wherein the organic carboxylic acid is at least one selected from the group consisting of citric acid, glycolic acid, malic acid, and tartaric acid.

6. The contact lens disinfecting solution of claim 1, wherein hydrogen peroxide is present at a concentration of 2 to 6 wt %.

7. The contact lens disinfecting solution of claim 1, further comprising at least one chelating agent selected from the group consisting of group consisting of EDTA, a salt thereof, etidronic acid, and a salt thereof.

8. The contact lens disinfecting solution of claim 7, wherein the chelating agent is present in the contact lens disinfecting solution at a concentration in the range of from 0.01 to 0.5 wt. %.

9. The contact lens disinfecting solution of claim 1, further comprising at least one of a surfactant and a nonionic tonicity agent.

10. The contact lens disinfecting solution of claim 1, further comprising a nonionic tonicity agent selected from the group consisting of propylene glycol, glycerol, and a saccharide.

11. The contact lens disinfecting solution of claim 1, further comprising a surfactant that is selected from the group consisting of polyethylene glycol ethers of higher alcohols, polyethylene glycol esters of higher fatty acids, polyglycerol esters of fatty acids, polyethylene glycol ethers of alkyl phenols, polyethylene glycol sorbitan alkyl esters, polyoxyethylene-polyoxypropylene glycols (poloxamers), and ethylenediamine tetrapolyoxyethylene polyoxypropylenes (poloxamines).

12. A contact lens disinfecting system, comprising:
    a metal catalyst that is capable of decomposing hydrogen peroxide; and
    a contact lens disinfecting solution, comprising:
    hydrogen peroxide at a concentration of 1 to 10 wt %; and
    at least one of an organic carboxylic acid and a salt thereof which comprises a hydroxyl group and a carboxyl group that are bonded to one carbon atom.

13. The contact lens disinfecting system of claim 12, wherein the organic carboxylic acid is at least one selected from the group consisting of citric acid, glycolic acid, malic acid, and tartaric acid.

14. The contact lens disinfecting system of claim 12, wherein the organic carboxylic acid is present in the contact lens disinfecting solution at a concentration of 0.1 wt % or more.

15. The contact lens disinfecting system of claim 12, wherein the organic carboxylic acid is present in the contact lens disinfecting solution at a concentration of 0.1 to 5 wt %.

16. The contact lens disinfecting system of claim 12, wherein the metal catalyst is selected from the group consisting of platinum, palladium, silver, copper, manganese, cobalt, aluminum, and oxides thereof.

17. The contact lens disinfecting system of claim 12, further comprising a treatment container that includes the metal catalyst.

18. The contact lens disinfecting system of claim 12, wherein the contact lens disinfecting solution has a pH of from 6 to 8.

* * * * *